United States Patent [19]

Böhner et al.

[11] 4,233,060
[45] Nov. 11, 1980

[54] α-PHENOXY-THIOLPROPIONIC ACIDS

[75] Inventors: Beat Böhner, Binningen; Otto Rohr, Therwil; Hermann Rempfler, Binningen, all of Switzerland; Georg Pissiotas, Lörach, Fed. Rep. of Germany

[73] Assignee: Ciba-Geigy Corporation, Ardsely, N.Y.

[21] Appl. No.: 962,517

[22] Filed: Nov. 20, 1978

[30] Foreign Application Priority Data

Nov. 24, 1977 [CH] Switzerland ............ 14398/77

[51] Int. Cl.$^3$ ............... C07C 153/23; C07D 213/62; C07D 295/08; C07D 295/14
[52] U.S. Cl. ......................... 71/94; 260/455 R; 546/301; 546/261; 546/340; 71/100; 544/108; 544/163
[58] Field of Search .............. 260/455 R; 546/301, 546/261, 340; 71/94, 100; 544/108, 163

[56] References Cited
U.S. PATENT DOCUMENTS

| 2,259,869 | 10/1941 | Allen | 260/455 R |
| 3,165,544 | 1/1965 | Tilles | 260/455 R |

Primary Examiner—Henry R. Jiles
Assistant Examiner—Robert C. Wittenbaugh
Attorney, Agent, or Firm—Harry Falber

[57] ABSTRACT

The present invention concerns new α-phenoxy-thiolpropionic acids and salts of the formula

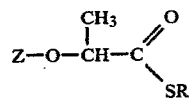

wherein R is hydrogen a metal cation or the cation of an amino- or ammonio-group, Z is a substituted phenyl or a substituted pyrid-2-yl radical.

These compounds have herbicidal activity by themselves but can be used as intermediats for the synthesis of more active derivatives.

8 Claims, No Drawings

α-PHENOXY-THIOLPROPIONIC ACIDS

The present invention relates to novel herbicidal α-phenoxy-thiolpropionic acids which are substituted in the para-position, and their salts, a process for their production, herbicidal compositions which contain the novel compounds as active ingredients, and a method of controlling weeds which comprises the use of the novel acids and salts or of compositions containing them, and the use of these compounds as intermediates for the synthesis of further herbicidal derivatives.

The compounds of the present invention have the formula I

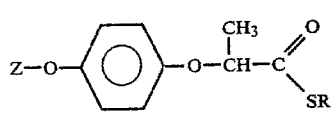

wherein R represents hydrogen, the equivalent of a metal cation or the equivalent of an amine or ammonio cation

wherein each of $R_2$, $R_3$, $R_4$ and $R_5$ independently represents hydrogen, alkyl, substituted alkyl, cycloalkyl, aralkyl or aryl, or two or three of the symbols $R_2$ to $R_5$, together with the nitrogen atom to which they are attached, form a heterocyclic ring, and Z represents either a substituted phenyl-(1) radical or a substituted pyridyl-(2) radical.

Eligible substituents of a phenyl-(1) radical are one or two members selected from the group consisting of halogen, $CF_3$, cyano and nitro. Substituents of a pyridyl-(2) radical Z are halogen and trifluoromethyl.

Preferred metal cations R are alkali metal and alkaline earth metal ions as well as the ions of Fe, Cu, Zn, Mn and Ni. It will be readily understood that polyvalent cations of the valency n are only bonded to the radical of the acid with the equivalent 1/n as radical R.

Of the many amines which, in protonised form, are suitable cations R, there may be mentioned in particular: ammonia, methylamine, dimethylamine, trimethylamine, tributylamine triethylamine, trihydroxyethylamine, dimethyl aniline, diethyl aniline, N,N-dimethylbenzylamine, pyridine, piperidine, morpholine, picolines etc.

Preferred substituted phenyl radicals Z are: 4-halogenophenyl, 2,4-dihalogenophenyl, 4-trifluoromethylphenyl, 2-halogeno-4-trifluoromethylphenyl, 4-cyanophenyl, 4-halogeno-2-cyanophenyl, 4-halogeno-2-nitrophenyl.

Especially preferred substituted pyridyl-(2) radicals Z of the formula

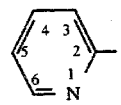

are: 5-halogenopyridyl-(2), 3,5-dihalogenopyridyl-(2), 5-trifluoromethylpyridyl-(2).

Preferred halogen substituents are bromine and, in particular, chlorine.

In addition to the use of the novel para-substituted α-phenoxy-thiolpropionic acids and their salts of the formula I as herbicides which are more active than the corresponding propionic acids (oxyacids), they can also be used as intermediates for the synthesis of other potent herbicides, namely corresponding thiolic acid derivatives, such as esters, amides etc.

A process for the production of the substituted α-phenoxy-thiolpropionic acids and their salts of the formula I comprises reacting an α-phenoxy-propionic acid halide of the formula II

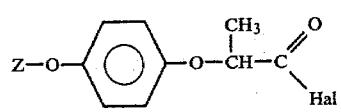

wherein Z is as defined in formula I and Hal represents a halogen atom, in particular a chlorine atom, in the presence of a basic acid acceptor, with hydrogen sulfide or a salt thereof, and isolating from the reaction mixture the resulting salt of the thiolic acid or, by acidification, the thiolic acid itself, and, if desired, converting this latter into a salt.

The reaction is preferably carried out in a solvent which is inert to the reactants. Suitable solvents for the reaction are those of the most widely different classes, such as aliphatic and aromatic hydrocarbons, and preferably polar organic solvents, such as alcohols, ethers, ketones, amides, stable esters, for example methyl ethyl ketone, dimethoxy ethane, dimethyl formamide, dimethyl sulfoxide, tetrahydrofurane etc. It is, however, also possible to use an organic base (amine) such as pyridine etc., as solvent, which then simultaneously acts as acid acceptor, whereupon the corresponding salt of the thiolpropionic acid forms in the reaction mixture.

As basic acid acceptors it is possible to use aqueous alkali metal hydroxides, such as KOH and NaOH as well as further conventional bases, for example ammonia, carbonates ($K_2CO_3$, $NaHCO_3$), alcoholates ($NaOCH_3$ and potassium tert-butylate), and also organic bases, such as triethylamine etc. If an organic base (e.g. pyridine) is used as solvent, it acts simultaneously as acid acceptor.

Instead of using gaseous hydrogen sulfide, with which certain solvents can also be saturated before the reaction, it is also possible to use a sulfide or hydrogen sulfide, for example $Na_2S$ or NaHS. Ordinarily a mineral acid, such as concentrated hydrochloric acid, is used for acidifying the reaction mixture, and the pH is adjusted to about 1.

The starting materials of the formula II, especially the α-phenoxy-propionic acid chlorides, can be most readily obtained in known manner from the corresponding free propionic acids by reaction with thionyl chloride ($SOCl_2$). The free nuclear-substituted α-phenoxy-propionic acids are known compounds which have been described, inter alia, in German Offenlegungsschriften No. 2,223,894, 2,546,251 and 2,652,384.

The preparation of the thiolic acids of the formula 1 usually resides in principle in the replacement of the hydroxyl group in oxyacids by the HS group, for which purpose further process variants which are described in Houben-Weyl, Vol. VIII, pp. 480 and 481 (1952) are possible. The reaction consists of an acylation of hydrogen sulfide.

Accordingly, the acid anhydrides can also be reacted in the presence of a base with gaseous $H_2S$, or acid chlorides can be reacted with $H_2S$ in the presence of an aluminium chloride catalyst. In addition, the reaction of araliphatic acid chlorides with cold alcoholic potassium hydrogen sulfide to produce thiolic acids is a further possibility.

Finally, a carbothiol group

can be introduced direct by treating Grignard compounds of the $R_1$-Mg-Hal type with carbon sulfoxide to produce, in addition to carbinols, the thiolic acids of the formula

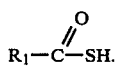

The following Examples illustrate a process for the production of a novel thiolic acid and a salt thereof. Further thiolic acids and their salts which are obtained in corresponding manner are listed in the following table.

cient stirring. The temperature is kept at 10° C. with an ice bath during the dropwise addition. The reaction mixture is subsequently stirred for 30 minutes at room temperature and poured into 500 ml of water. The cloudy, brown solution is adjusted to pH 1 with conc. hydrochloric acid, whereupon a brown oil precipitates. The oil is taken up in methylene chloride, and the organic phase is applied direct to a small column of silica gel and eluted with methylene chloride. The light yellow solution is evaporated, affording 34 g (99.4%) of α-[4-(4'-trifluoromethylphenoxy)-phenoxy] thiolpropionic acid in the form of a clear, orange oil with a refractive index $n_D^{21} = 1.5421$.

EXAMPLE 2

13.7 g (0.04 mole) of the thiolic acid obtained in Example 1 are dissolved in 20 ml of ether and 3.2 g (0.0405 mole) of pyridine are added to the solution. The reaction mixture is warmed for 2 hours to 40° C. and then concentrated. The residual clear, organic oil is triturated with hexane to form yellow crystals. The crystals are collected by filtration and dried at 40° C., affording 6.5 g of the pyridinium salt of α-[4-(4'-trifluoromethylphenoxy)-phenoxy thiolpropionic acid in the form of yellow crystals with a melting point of 82°-83° C.

The following compounds were obtained in analogous manner:

| Compound | Z | R | physical constant $n_D^{21}$ or melting point (°C.) |
|---|---|---|---|
| 1 | 4-trifluoromethylphenyl | H | $n_D^{21} = 1.5421$ |
| 2 | 4-chlorophenyl | H | $n_D^{21} = 1.5838$ |
| 3 | 2,4-dichlorophenyl | H | |
| 4 | 2-chloro-4-trifluoromethylphenyl | H | $n_D = 1.5520$ |
| 5 | 3,5-dichloro-pyridyl-(2) | H | $n_D = 1.5787$ |
| 6 | 4-trifluoromethylphenyl |  | m.p. = 82°-83° |
| 7 | " | 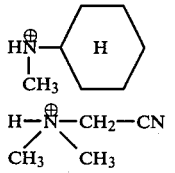 | m.p. = 114°-116° |
| 8 | " | H—N⊕—CH₂—CN with CH₃, CH₃ | $n_D = 1.5282$ |
| 9 | 3,5-dichloro-pyridyl-(2) | HN⊕—H with CH₃, CH₃ | $n_D = 1.5881$ |
| 10 | 2-nitro-4-chlorophenyl | H | |
| 11 | 5-chloro-pyridyl-(2) | H | |
| 12 | 2-chloro-4-bromphenyl | H | |
| 13 | 5-trifluoromethyl-pyridyl-(2) | H | |
| 14 | 2-cyano-4-chlorophenyl | H | |
| 15 | 4-cyanophenyl | H | |
| 16 | 2,4-dichlorophenyl | Na | m.p. >320° |
| 17 | 4-trifluorophenyl | K | m.p. >320° |

EXAMPLE 1

34.5 g (0.1 mole) of α-[4-(4'-trifluoromethyl-phenoxy)-phenoxy] propionic acid chloride are added dropwise to a mixture of 17.9 g of 85% KOH in 8.9 ml of water and 150 ml of dimethoxy ethane that has been saturated beforehand at 10°-15° C. with $H_2S$ with effi- In addition to their usefulness as herbicidal active substances, the novel thiolic acids and their salts of the formula I are also important intermediates for the production of herbicidal thiolpropionates, some of which are known and described for example in German Offenlegungsschriften Nos. 2,223,894 and 2,531,643, but which up till now have been obtained by a different route.

The thiolpropionic acids of the present invention and their salts constitute a novel group of derivatives of α-[4-(phenovxy)-phenoxy] thiolcarboxylic acid and α-[4-(pyridyloxy)-phenoxy] thiolcarboxylic acid which, in relatively low rates of application, exhibit a strong herbicidal action and/or influence plant growth in another agriculturally useful manner.

The active substances of the formula I can be used as herbicides both in pre-emergent and, in particular, in post-emergent application. Their action is directed in particular against monocotyledonous weeds; but they can also be used for inhibiting the growth of dicotyledonous plants.

The active substances of the formula I have a low toxicity to warm blooded animals. The rates of application are advantageously between 0.1 and 5 kg of active substance per hectare.

The present invention also provides herbicidal compositions and compositions for regulating plant growth which contain a compound of the formula I as active component. Such compositions can be processed in the conventional manner to solid formulations (dusts, tracking powders, granulates) and to concentrates which are dispersible in water (wettable powders, emulsions, emulsifiable concentrates and pastes) or to solutions, and are formulated by known methods with appropriate adjuvants and carriers.

What is claimed is:

1. A compound of the formula

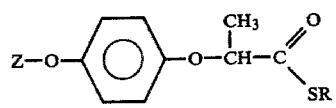

wherein R represents hydrogen, a metal cation or an amine or ammonio cation

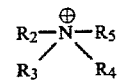

wherein each of $R_2$, $R_3$, $R_4$, $R_5$ independently represents hydrogen, $C_1$–$C_4$ alkyl, $C_1$–$C_4$ alkyl substituted by hydrogen or cyano, cyclohexyl, phenyl or benzyl, or two or three of the symbols $R_2$ to $R_5$, together with the nitrogen to which they are attached form a pyridine, piperidine, morpholine or picoline ring; and Z represents phenyl substituted by halogen, trifluoromethyl, cyano or nitro, or pyridyl substituted by halogen or trifluoromethyl, and the physiologically acceptable salts thereof.

2. The compound of claim 1, wherein said phenyl group in Z is substituted in the 4-position.

3. The compound of claim 2, wherein said phenyl group is also substituted in the 2-position.

4. The compound of claim 1, wherein said pyridyl group in Z is substituted in the 5-position.

5. The compound of claim 4, wherein said pyridyl group is also substituted in the 3-position.

6. α-[4-(4'-Trifluoromethylphenoxy)-phenoxy] thiolpropionic acid and the pyridinium salt thereof according to claim 1.

7. A herbicidal composition which contains, as active component, a herbicidally effective amount of an α-phenoxy-thiolpropionic acid or salt thereof of claim 1, together with a suitable carrier therefor.

8. A method of combatting weeds at a locus, which comprises applying to said locus a herbicidally effective amount of a phenoxy-thiolpropionic acid or a salt thereof of claim 1.

* * * * *